United States Patent
Andersch et al.

(10) Patent No.: US 7,745,375 B2
(45) Date of Patent: Jun. 29, 2010

(54) SYNERGISTIC INSECTICIDE MIXTURES

(75) Inventors: Wolfram Andersch, Bergisch Gladbach (DE); Peter Jeschke, Bergisch Gladbach (DE); Wolfgang Thielert, Odenthal (DE)

(73) Assignee: Bayer CropScience AG, Monheim (DE)

( * ) Notice: Subject to any disclaimer, the term of this patent is extended or adjusted under 35 U.S.C. 154(b) by 754 days.

(21) Appl. No.: 10/575,276

(22) PCT Filed: Sep. 30, 2004

(86) PCT No.: PCT/EP2004/010912

§ 371 (c)(1), (2), (4) Date: Apr. 11, 2006

(87) PCT Pub. No.: WO2005/036966

PCT Pub. Date: Apr. 28, 2005

(65) Prior Publication Data

US 2007/0078171 A1  Apr. 5, 2007

(30) Foreign Application Priority Data

Oct. 13, 2003  (DE) .................. 103 47 440

(51) Int. Cl.
*A01N 43/64* (2006.01)
(52) U.S. Cl. .................. 504/134; 504/139; 504/141
(58) Field of Classification Search ............ 514/340
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,742,060 A | 5/1988 | Shiokawa et al. | |
| 4,808,430 A | 2/1989 | Kouno | |
| 4,849,432 A | 7/1989 | Shiokawa et al. | |
| 5,876,739 A | 3/1999 | Turnblad et al. | |
| 6,114,362 A | 9/2000 | Dutzmann et al. | |
| 6,297,263 B1 | 10/2001 | Dutzmann et al. | |
| 6,306,414 B1 | 10/2001 | Koike | |
| 6,423,726 B2 | 7/2002 | Dutzmann et al. | |
| 6,444,667 B1* | 9/2002 | Andersch et al. | 514/229.2 |
| 6,479,542 B2 | 11/2002 | Sembo et al. | |
| 7,008,903 B2 | 3/2006 | Dutzmann et al. | |
| 2001/0046986 A1* | 11/2001 | Miura et al. | 514/211.03 |
| 2002/0173529 A1 | 11/2002 | Dutzmann et al. | |
| 2002/0193352 A1 | 12/2002 | Erdelen et al. | |
| 2003/0013684 A1* | 1/2003 | Kawahara et al. | 514/75 |
| 2003/0176428 A1 | 9/2003 | Schneidersmann et al. | |
| 2003/0232821 A1 | 12/2003 | Maienfisch et al. | |
| 2005/0009703 A1 | 1/2005 | Wachendorff-Neumann et al. | |
| 2005/0009883 A1 | 1/2005 | Uhr et al. | |
| 2005/0101639 A1 | 5/2005 | Ammermann et al. | |
| 2006/0004070 A1 | 1/2006 | Wachendorff-Neumann et al. | |
| 2006/0014738 A1 | 1/2006 | Wachendorff-Neumann et al. | |
| 2006/0035942 A1 | 2/2006 | Wachendorff-Neumann et al. | |
| 2006/0079401 A1 | 4/2006 | Dutzmann et al. | |
| 2006/0276342 A1 | 12/2006 | Krahmer et al. | |
| 2007/0037799 A1 | 2/2007 | Dahmen et al. | |
| 2007/0054804 A1 | 3/2007 | Suty-Heinze | |
| 2007/0142327 A1 | 6/2007 | Funke et al. | |
| 2007/0155797 A1 | 7/2007 | Andersch et al. | |
| 2007/0203025 A1 | 8/2007 | Bickers et al. | |
| 2007/0213396 A1 | 9/2007 | Thielert et al. | |
| 2007/0232598 A1 | 10/2007 | Funke et al. | |
| 2007/0270416 A1 | 11/2007 | Funke et al. | |
| 2008/0027114 A1 | 1/2008 | Funke et al. | |
| 2008/0070863 A1 | 3/2008 | Funke et al. | |
| 2008/0261811 A1 | 10/2008 | Krohn et al. | |
| 2008/0269051 A1 | 10/2008 | Suty-Heinze et al. | |
| 2008/0269263 A1 | 10/2008 | Dahmen et al. | |
| 2008/0274882 A1 | 11/2008 | Krohn et al. | |

FOREIGN PATENT DOCUMENTS

| | | |
|---|---|---|
| EP | 0 192 060 A1 | 8/1986 |
| EP | 0 235 725 B1 | 9/1987 |
| EP | 0 302 389 B1 | 2/1989 |
| EP | 0 376 279 B1 | 7/1990 |
| EP | 0 580 553 B1 | 1/1994 |
| EP | 0 649 845 B1 | 4/1995 |
| WO | WO 91/04965 A1 | 4/1991 |
| WO | WO 97/40692 A1 | 11/1997 |
| WO | WO 02/17720 A1 | 3/2002 |
| WO | WO 02/28186 A2 | 4/2002 |
| WO | WO 02/080675 A1 | 10/2002 |

OTHER PUBLICATIONS

Nauen R., Thiamethoxam is a neonicotinoid precursor converted to clothianidin in insects and plants, Pesticide Biochemistry and Physiology 76 (2003) 55-69.*

Millstone, E., "Food additives: the balance of risks and benefits," *Chem. Ind.*:730-733, Society of Chemical Industry (1985).

European Patent Opposition, European Patent No. 1675462 B1, European Patent Office, mailed on Mar. 2, 2009.

Bauer, T.A., et al., "Response of Selected Weed Species to Postemergence Imazethapyr and Bentazon," *Weed Tech.* 9:236-242, The Weed Science Society of America (1995).

Blackshaw, R.E., et al., "Herbicide Combinations for Postemergent Weed Control in Safflower (*Carthamus tinctorius*)," *Weed Tech.* 4:97-104, The Weed Science Society of America (1990).

Blackshaw, R.E., "HOE-39866 Use in Chemical Fallow Systems," *Weed Tech.* 3:420-428, The Weed Science Society of America (1989).

Blackshaw, R.E., "Synergistic Mixes of DPX-A7881 and Clopyralid in Canola (*Brassica napus*)," *Weed Tech.* 3:690-695, The Weed Science Society of America (1989).

Blouin, D.C., et al., "Analysis of Synergistic and Antagonistic Effects of Herbicides Using Nonlinear Mixed-Model Methodology," *Weed Tech.* 18:464-472, The Weed Science Society of America (2004).

(Continued)

*Primary Examiner*—Johann R Richter
*Assistant Examiner*—Danielle Sullivan
(74) *Attorney, Agent, or Firm*—Sterne, Kessler, Goldstein & Fox P.L.L.C.

(57) ABSTRACT

The invention relates to insecticidal mixtures comprising, as active compounds, in each case two compounds from the series of the chloronicotinyl insecticides, and to the use of these mixtures for controlling animal pests.

10 Claims, No Drawings

OTHER PUBLICATIONS

Bradley, P.R., et al., "Response of Sorghum (*Sorghum bicolor*) to Atrazine, Ammonium Sulfate, and Glyphosate," *Weed Tech. 14*:15-18, The Weed Science Society of America (2000).

Buker, III, R.S., et al., "Confirmation and Control of a Paraquat-Tolerant Goosegrass (*Eleusine indica*) Biotype," *Weed Tech. 16*:309-313, The Weed Science Society of America (2002).

Burke, I.C., et al., "CGA-362622 Antagonizes Annual Grass Control with Clethodim," *Weed Tech. 16*:749-754, The Weed Science Society of America (2002).

Flint, J.L., et al., "Analyzing Herbicide Interactions, A Statistical Treatment of Colby's Method," *Weed Tech. 2*:304-309, The Weed Science Society of America (1988).

Gillespie, G.R., and Nalewaja, J.D., "Wheat (*Triticum aestivum*) Response to Triallate Plus Chlorsulfuron," *Weed Tech. 3*:20-23, The Weed Science Society of America (1989).

Green, J.M., et al., "Metribuzin and Chlorimuron Mixtures for Preemergence Broadleaf Weed Control in Soybeans, *Glycine max*," *Weed Tech. 2*:355-363, The Weed Science Society of America (1988).

Harker, N.K., and O'Sullivan, P.A., "Synergistic Mixtures of Sethoxydim and Fluazifop on Annual Grass Weeds," *Weed Tech. 5*:310-316, The Weed Science Society of America (1991).

Kent, L.M., et al., "Effect of Ammonium Sulfate, Imazapyr, and Environment on the Phytotoxicity of Imazethapyr," *Weed Tech. 5*:202-205, The Weed Science Society of America (1991).

Kotoula-Syka, E., et al., "Interactions between SAN 582H and Selected Safeners on Grain Sorghum (*Sorghum bicolor*) and Corn (*Zea mays*)," *Weed Tech. 10*:299-304, The Weed Science Society of America (1996).

Lanclos, D.Y., et al., "Glufosinate Tank-Mix Combinations in Glufosinate-Resistant Rice (*Oryza sativa*)," *Weed Tech. 16*:659-663, The Weed Science Society of America (2002).

Norris, J.L., et al., "Weed Control from Herbicide Combinations with Three Formulations of Glyphosate," *Weed Tech. 15*:552-558, The Weed Science Society of America (2001).

Novosel, K.M., et al., "Metolachlor Efficacy as Influenced by Three Acetolactate Synthase-Inhibiting Herbicides," *Weed Tech. 12*:248-253, The Weed Science Society of America (1998).

Palmer, E.W., et al., "Broadleaf Weed Control in Soybean (*Glycine max*) with CGA-277476 and Four Postemergence Herbicides," *Weed Tech. 14*:617-623, The Weed Science Society of America (2000).

Salzman, F.P., and Renner, K.A., "Response of Soybean Combinations of Clomazone, Metribuzin, Linuron, Alachlor, and Atrazine," *Weed Tech. 6*:922-929, The Weed Science Society of America (1992).

Scott, R.C., et al., "Spray Adjuvant, Formulation, and Environmental Effects of Synergism from Post-Applied Tank Mixtures of SAN 582H with Fluazifop-P, Imazethapyr, and Sethoxydim," *Weed Tech. 12*:463-469, The Weed Science Society of America (1998).

Shaw, D.R. And Arnold, J.C., "Weed Control from Herbicide Combinations with Glyphosate," *Weed Tech. 16*:1-6, The Weed Science Society of America (2002).

Snipes, C.E., and Allen, R.L., "Interaction of Graminicides Applied in Combination with Pyrithiobac," *Weed Tech. 10*:889-892, The Weed Science Society of America (1996).

Wehtje, G. and Walker, R.H., "Interaction of Glyphosate and 2,4-DB for the Control of Selected Morningglory (*Ipomoea* spp.) Species," *Weed Tech. 11*:152-156, The Weed Science Society of America (1997).

Zhang, W., et al., "Fenoxaprop Interactions for Barnyardgrass (*Echinochloa crus-galli*) Control in Rice," *Weed Tech. 19*:293-297, The Weed Science Society of America (2005).

Co-pending U.S. Appl. No. 10/581,348 inventors Funke, C., et al., filed on Nov. 20, 2004 (Not Published).

Co-pending U.S. Appl. No. 11/910,659 inventors Wachendorff-Neumann, U., et al., filed on Mar. 27, 2007 (Not Published).

Co-pending U.S. Appl. No. 12/515,339 inventors Dutzmann, S., et al., filed on May 18, 2009 (Not Published).

Colby, S.R., "Calculating Synergistic and Antagonistic Responses of Herbicide Combinations," *Weeds 15*:20-22, Weed Society of America (1967).

Esp@cenet database, English language abstract for JP 2003-063911 A2.

STN Database, Accession No. 2003:166933, English language abstract for JP 2003-063911 A2.

International Search Report for International Application No. PCT/EP2004/010912, European Patent Office, Netherlands, mailed on Feb. 15, 2005.

* cited by examiner

SYNERGISTIC INSECTICIDE MIXTURES

The present invention relates to novel active compound combinations which comprise, as active compounds, in each case two compounds from the series of the chloronicotinyl insecticides and which have very good insecticidal properties.

It is already known that chloronicotinyl insecticides can be employed for controlling animal pests, in particular insects. The chloronicotinyl insecticides include the following compounds:

imidacloprid, of the formula (I)

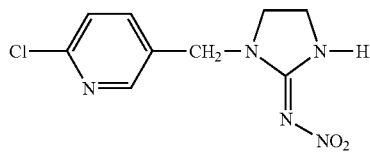

(cf. EP 0 192 060), clothianidin, of the formula (II),

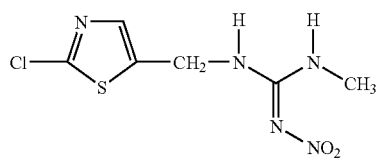

(EP 0 376 279)

dinotefuran, of the formula (III),

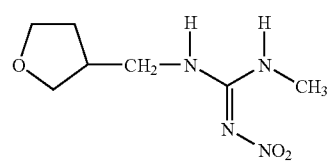

(EP 0 649 845)

thiamethoxam, of the formula (IV),

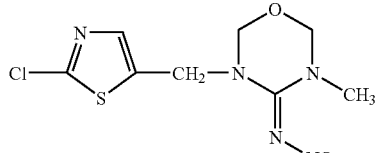

(EP 0 580 553)

thiacloprid, of the formula (V)

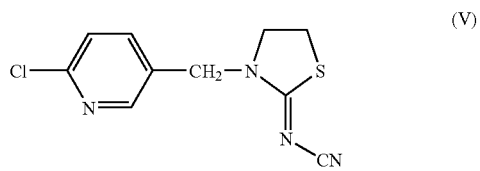

(EP 0 235 725)

acetamiprid, of the formula (VI),

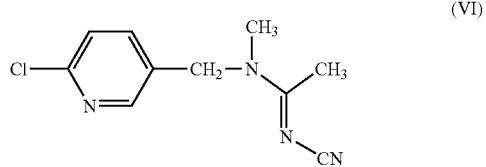

(WO 91/04965)

nitenpyram, of the formula (VII),

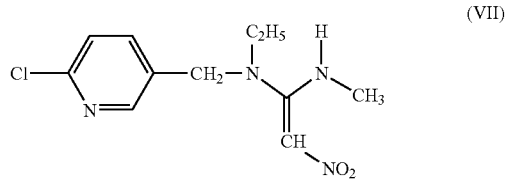

(EP 0 302 389)

While the activity of these compounds is good, it leaves something to be desired in some cases when the compounds are employed at low application rates or against specific pests.

It has now been found that mixtures comprising in each case at least two and in particular precisely two compounds from the series of the chloronicotinyl insecticides, in particular those of the formulae (I) to (VII), act synergistically and are suitable for controlling animal pests. Owing to this synergism, markedly lower amounts of active compound can be used, i.e. the activity of the mixture is greater than the activity of the individual components.

The ratio between the two active compounds employed and the total amount of mixture to be applied depends on the species and the occurrence of the insects or Acarina and can be varied within a wide range. The optimal ratios and total application rates can be determined for each application by test series.

The following mixtures according to the invention may be mentioned specifically:

TABLE

| Mixture No. | First active compound | Second active compound | Preferred mixing ratio | Particularly preferred mixing ratio |
|---|---|---|---|---|
| 1 | imidacloprid | clothianidin | 100:1-1:100 | 10:1-1:10 |
| 2 | imidacloprid | dinotefuran | " | " |
| 3 | imidacloprid | thiamethoxam | " | " |
| 4 | imidacloprid | thiacloprid | " | " |
| 5 | imidacloprid | acetamiprid | " | " |
| 6 | imidacloprid | nitenpyram | " | " |

TABLE-continued

| Mixture No. | First active compound | Second active compound | Preferred mixing ratio | Particularly preferred mixing ratio |
|---|---|---|---|---|
| 7 | clothianidin | dinotefuran | " | " |
| 8 | clothianidin | thiamethoxam | " | " |
| 9 | clothianidin | thiacloprid | " | " |
| 10 | clothianidin | acetamiprid | " | " |
| 11 | clothianidin | nitenpyram | " | " |
| 12 | dinotefuran | thiamethoxam | " | " |
| 13 | dinotefuran | thiacloprid | " | " |
| 14 | dinotefuran | acetamiprid | " | " |
| 15 | dinotefuran | nitenpyram | " | " |
| 16 | thiamethoxam | thiacloprid | " | " |
| 17 | thiamethoxam | acetamiprid | " | " |
| 18 | thiamethoxam | nitenpyram | " | " |
| 19 | thiacloprid | acetamiprid | " | " |
| 20 | thiacloprid | nitenpyram | " | " |
| 21 | acetamiprid | nitenpyram | " | " |

The active compound combinations are well tolerated by plants, have favourable toxicity to warm-blooded species and are suitable for controlling animal pests, in particular insects, arachnids and nematodes which are found in agriculture, in forests, in the protection of stored products and materials, and in the hygiene sector. They can preferably be employed as plant protection agents. They are effective against normally sensitive and resistant species and against all or individual developmental stages. The abovementioned pests include:

From the order of the *Isopoda*, for example *Oniscus asellus, Armadillidium vulgare, Porcellio scaber*.

From the order of the *Diplopoda*, for example *Blaniulus guttulatus*.

From the order of the *Chilopoda*, for example *Geophilus carpophagus, Scutigera* spp.

From the order of the *Symphyla*, for example *Scutigerella immaculata*.

From the order of the *Thysanura*, for example *Lepisma saccharina*.

From the order of the *Collembola*, for example *Onychiurus armatus*.

From the order of the *Orthoptera*, for example *Acheta domesticus, Gryllotalpa* spp., *Locusta migratoria migratorioides, Melanoplus* spp., *Schistocerca gregaria*.

From the order of the *Blattaria*, for example *Blatta orientalis, Periplaneta americana, Leucophaea maderae, Blattella germanica*.

From the order of the *Dermaptera*, for example *Forficula auricularia*.

From the order of the *Isoptera*, for example *Reticulitermes* spp.

From the order of the *Phthiraptera*, for example *Pediculus humanus corporis, Haematopinus* spp., *Linognathus* spp., *Trichodectes* spp., *Damalinia* spp.

From the order of the *Thysanoptera*, for example *Hercinothrips femoralis, Thrips tabaci, Thrips palmi, Frankliniella occidentalis*.

From the order of the *Heteroptera*, for example *Eurygaster* spp., *Dysdercus intermedius, Piesma quadrata, Cimex lectularius, Rhodnius prolixus, Triatoma* spp.

From the order of the *Homoptera*, for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pempbigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp., *Psylla* spp.

From the order of the *Lepidoptera*, for example *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*.

From the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus*.

From the order of the *Hymenoptera*, for example *Diprion* spp., *Hoplocampa* spp., *Lasius* spp., *Monomorium pharaonis, Vespa* spp.

From the order of the *Diptera*, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the *Siphonaptera*, for example *Xenopsylla cheopis, Ceratophyllus* spp.

From the class of the *Arachnida*, for example *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

All plants and plant parts can be treated in accordance with the invention. Plants are understood as meaning, in the present context, all plants and plant populations, such as desired and undesired wild plants or crop plants (including naturally occurring crop plants). Crop plants may be plants which can be obtained by conventional breeding and optimization methods or by biotechnological and genetic engineering methods or by combinations of these methods, including the transgenic plants and including the plant varieties capable or not capable of being protected by plant breeders' rights.

Plant plants are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

What may be emphasized in this context is the particularly advantageous effect of the compositions according to the invention with regard to their use in cereal plants such as, for example, wheat, oats, barley, spelt, triticale and rye, but also in maize, sorghum and millet, rice, sugar cane, soya beans, sunflowers, potatoes, cotton, oilseed rape, canola, tobacco, sugar beet, fodder beet, asparagus, hops and fruit plants (comprising pome fruit such as, for example, apples and pears, stone fruit such as, for example, peaches, nectarines, cherries, plums and apricots, citrus fruits such as, for example, oranges, grapefruits, limes, lemons, kumquats, tangerines and satsumas, nuts such as, for example, pistachios, almonds, walnuts and pecan nuts, tropical fruits such as, for example, mango, paw-paw, pineapple, dates and bananas, and grapes) and vegetables (comprising leaf vegetables such as, for example, endives, corn salad, Florence fennel, lettuce, cos lettuce, Swiss chard, spinach and chicory for salad use, cabbages such as, for example, cauliflower, broccoli, Chinese leaves, *Brassica oleracea* (L.) convar. *acephala* var. *sabellica* L. (curly kale, feathered cabbage), kohlrabi, Brussels sprouts, red cabbage, white cabbage and savoy cabbage, fruit vegetables such as, for example, aubergines, cucumbers, capsicums, table pumpkins, tomatoes, courgettes and sweetcorn, root vegetables such as, for example celeriac, wild turnips, carrots, including yellow cultivars, *Raphanus sativus* var. *niger* and var. *radicula*, beetroot, scorzonera and celery, legumes such as, for example, peas and beans, and vegetables from the Allium family such as, for example, leeks and onions).

The treatment according to the invention of the plants and plant parts with the active compound combinations is carried out either directly or by treating their environment, habitat or store by the customary treatment methods, for example by dipping, spraying, vaporizing, misting, broadcasting, painting on and, in the case of propagation material, in particular seeds, furthermore by coating with one or more layers.

The mixtures according to the invention are particularly suitable for the treatment of seeds. Thus, most of the damage to crop plants which is caused by pests occurs as early as when the seed is infested during storage and after the seed is introduced into the soil, and during and immediately after germination of the plants. This phase is particularly critical since the roots and shoots of the glowing plants are particularly sensitive and even minor damage can lead to the death of the whole plant. Protecting the seed and the germinating plant by the use of suitable compositions is therefore of particularly great interest.

The control of pests by treating the seed of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection products after planting or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection products being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the germinating plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plant after emergence, from pests. In this manner, the immediate treatment of the crop at the time of sowing or shortly thereafter can be dispensed with.

A further advantage is the synergistically increased insecticidal activity of the compositions according to the invention in comparison with the respective individual active compound, which exceeds the total of the activity of the two active compounds when applied individually. This makes possible an optimization of the amount of active compound employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can already be controlled by the expression of the for example insecticidal protein, and, surprisingly, the result in addition is a synergistically complemented activity together with the compositions according to the invention, which, again, increases the efficacy of the protection against attack by pests.

The compositions according to the invention are suitable for protecting seed of any plant variety as already mentioned above which is employed in agriculture, in the greenhouse, in forests, in horticulture or in viticulture. In particular, this takes the form of seed of maize, peanut, canola, oilseed rape, poppy, olive, coconut, cacao, soya beans, cotton, beet (for example sugar beet and fodder beet), rice, sorghum and millet, wheat, barley, oats, rye, sunflower, sugar cane or tobacco. The compositions according to the invention are likewise suitable for treating the seed of fruit plants and vegetables as already mentioned above. The treatment of the seed of maize, soya beans, cotton, wheat and canola or oilseed rape is of particular importance. Thus, for example, the mixture according to the invention which comprises the active compound methiocarb and imidacloprid is particularly suitable for treating the seed of maize.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

Within the scope of the present invention, the composition according to the invention is applied to the seed either alone or in suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. As a rule, it is preferable to apply the composition to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations can be converted into the customary formulations, such as solutions, emulsions, wettable powders, suspensions, powders, dusts, pastes, soluble powders, granules, suspoemulsion concentrates, natural and synthetic materials impregnated with active compounds and microencapsulations in polymeric materials.

These formulations are produced in a known manner, for example by mixing the active compounds with extenders, that is, liquid solvents and/or solid carriers, optionally with the use of surface-active agents, that is, emulsifiers and/or dispersants and/or foam formers.

If water is used as extender, auxiliary solvents which can be used are, for example, organic solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and ethers and esters, ketones, such as acetone, methyl ethyl ketone, methyl isobutyl ketone or cyclohexanone, strongly polar solvents, such as dimethylformamide and dimethyl sulphoxide, and water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; as emulsifiers and/or foam formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; as dispersants there are suitable: for example lignosulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compound, preferably between 0.5 and 90%.

Preferably, the active compound combinations according to the invention comprise no further active compounds apart from the two chloronicotinyl insecticides of the formulae (I) to (VII).

If appropriate, the active compound combinations according to the invention, in commercially available formulations and in the use forms prepared from these formulations, can be present in a mixture with other known active compounds such as insecticides, attractants, sterilants, bactericides, acaricides, nematicides, fungicides, growth regulators or herbicides. The insecticides include, for example, phosphoric esters, carbamates, carboxylic esters, chlorinated hydrocarbons, phenylureas, substances produced by microorganisms, and the like.

Examples of especially advantageous components in the mixtures are the following:

Fungicides:

aldimorph, ampropylfos, ampropylfos-potassium, andoprim, anilazin, azaconazole, azoxystrobin, benalaxyl, benodanil, benomyl, benzamacril, benzamacryl-isobutyl, bialaphos, binapacryl, biphenyl, bitertanol, blasticidin-s, bromuconazole, bupirimate, buthiobate, calcium polysulphide, capsimycin, captafol, captan, carbendazim, carboxin, carvon, quinomethionate, chlobenthiazon, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazol, diclofluanid, diclomezin, dicloran, diethofencarb, difenoconazole, dimethirimol, dimethomorph, diniconazole, diniconazole-M, dinocap, diphenylamin, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzon, fluazinam, flumetover, fluoromid, fluquinconazole, flurprimidol, flusilazole, flusulfamid, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine-albesilate, iminoctadine-triacetate, iodocarb, ipconazole, iprobenfos (IBP), iprodione, irurnamycin, isoprothiolan, isovaledione, kasugamycin, kresoxim-methyl, copper preparations such as: copper hydroxide, copper naphthenate, copper oxychloride, copper sulphate, copper oxide, oxine-copper and Bordeaux mixture, mancopper, mancozeb, maneb, meferinizone, mepanipyrim, mepronil, metalaxyl, metconazole, methasulfocarb, methfroxam, metiram, metomeclam, metsulfovax, mildiomycin, myclobutanil, myclozolin, nickel dimethyldithiocarbarnate, nitrothal-isopropyl, nuarimol, ofurace, oxadixyl, oxamocarb, oxolinic acid, oxycarboxirn, oxyfenthiin, paclobutrazole, pefurazoate, penconazole, pencycuron, phosdiphen, pimaricin, piperalin, polyoxine, polyoxorim, probenazole, prochloraz, procymidon, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamid, zineb, ziram and Dagger G,

OK-8705,

OK-8801,

α-(1,1-dimethylethyl)-β-(2-phenoxyethyl)-1H-1,2,4-triazole-1-ethanol,

α-2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)phenyl]methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxyphenylacetamide, 1-isopropyl {2-methyl-1-[[[1-(4-methylphenyl)ethyl]amino]carbonyl]propyl}carbamate 1-(2,4-dichlorophenyl)-2-(1H-1,2,4-triazol-1-yl)ethanone O-(phenylmethyl)oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodmethyl)sulphonyl]4-methylbenzene, 1-[[2-(2,4-dichlorophenyl)-1,3-dioxolan-2-yl]methyl]-1H-imidazole, 1-[[2-(4-chlorophenyl)-3-phenyloxiranyl]methyl]-1H-1,2,4-triazole, 1-[1-[2-[(2,4-dichlorophenyl)methoxy]phenyl]ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,2-dichloro-N-[1-(4-chlorophenyl)ethyl]-1-ethyl-3-methylcyclopropanecarboxamide, 2,6-dichloro-5-(methylthio)-4-pyrimidinyl thiocyanate, 2,6-dichloro-N-4-trifluoromethylbenzyl)benzamide, 2,6-dichloro-N-[[4-(trifluoromethyl)phenyl]methyl]benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-α-D-glucopyranosyl]amino]4-methoxy-1H-pyrrolo[2,3-d]pyrimidine-5-carbonitrile, 2-aminobutane, 2-bromo-2-(bromomethyl)pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)acetamide, 2-phenylphenol(OPP), 3,4-dichloro-1-[4-(difluoromethoxy)phenyl]-1H-pyrrole-2,5-dione, 3,5-dichloro-N-[cyano[(1-methyl-2-propynyl)oxy]methyl]benzamide, 3-(1,1-dimethylpropyl-1-oxo)-1H-indene-2-carbonitrile, 3-[2-(4-chlorophenyl)-5-ethoxy-3-isoxazolidinyl]pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, N-2-[(phenylamino)carbonyl]-9H-xanthene-9-carbonhydrazide, bis-(1-methylethyl)-3-methyl-4-[(3-methylbenzoyl)oxy]-2,5-thiophene dicarboxylate, cis-1-(4-chlorophenyl)-2-(1H-1,2,4-triazol-1-yl)cycloheptanol, cis-4-[3-[4-(1,1-diethylpropyl)phenyl-2-methylpropyl]-2,6-dimethylmorpholine hydrochloride, ethyl [(4-chlorophenyl)azo]cyanoacetate, potassium hydrogencarbonate, sodium methane tetrathiolate, methyl 1-(2,3-dihydro-2,2-dimethyl-1H-inden-1-yl)-1H-imidazole-5-carboxylate, methyl N-(2,6-dimethylphenyl)-N-5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methylcyclohexanecarboxamide, N-(2,6-dimethylphenyl)-2-methoxy-N-(tetrahydro-2-oxo-3-furanyl)acetamide, N-(2,6-dimethylphenyl)-2-methoxy-N-(tetrabydro-2-oxo-3-thienyl)acetamide, N-(2-chloro-4-nitrophenyl)-4-methyl-3-nitrobenzenesulphonamide, N-(4-cyclohexylphenyl)-1,4,5,6-tetrahydro-2-pyrimidineamine, N-(4-hexylphenyl)-1,4,5,6-tetrahydro-2-pyrimidineamine, N-(5-chloro-2-methylphenyl)-2-methoxy-N-2-oxo-3-oxazolidinyl)acetamide, N-(6-methoxy)-3-pyridinyl)cyclopropanecarboxamide, N-[2,2,2-trichloro-1-[(chloracetyl)amino]ethyl]benzamide, N-[3-chloro-4,5-bis-(2-propinyloxy)phenyl]-N'-methoxymethaneimidamide, sodium N-formyl-N-hydroxy-DL-alaninate, O,O-diethyl [2-(dipropylamino)-2-oxoethyl]ethylphosphoramidothioate, O-methyl S-phenyl phenylpropylphosphoramidothioate, S-methyl 1,2,3-benzothiadiazole-7-carbothioate, spiro[2H]-1-benzopyran-2,1'(3'H)-isobenzofuran]-3'-one.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides

1. Acetylcholine Esterase (AChE) Inhibitors 1.1 Carbamates, for Example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb Triazamates 1.2 Organophosphates, for Example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion 2. Sodium Channel Modulators/Voltage-Dependent Sodium Channel Blockers 2.1 Pyrethroids, for Example acrinathrin, allethrin (d-cis-trans, d-trans), beta-cyfluthrin, bifenthrin, bioallethrin, bioallethrin-S cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermetbrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (IR isomer), tralomethrin, transfluthrin, ZXI 8901, pyrethrins (pyrethrum)

DDT 2.2 Oxadiazines, for Example Indoxacarb

3. Acetylcholine Receptor Agonists/Antagonists 3.1 Chloronicotinyls, for Example acetamiprid, clothianidin, dinotefuran, imidacloprid, nitenpyram, nithiazine, thiacloprid, thiamethoxam 3.2 Nicotine, Bensultap, Cartap 4. Acetylcholine Receptor Modulators 4.1 Spinosyns, for Example Spinosad 5. GABA-Controlled Chloride Channel Antagonists 5.1 Cyclodiene Organochlorines, for Example camphechlor, chlordane, endosulfan, gamma-HCH, HCH, heptachlor, lindane, methoxychlor 5.2 Fiproles, for Example acetoprole, ethiprole, fipronil, vaniliprole 6. Chloride Channel Activators 6.1 Mectins, for Example avermectin, emamectin, emamectin-benzoate, ivermectin, milbemycin 7. Juvenile Hormone Mimetics, for Example diofenolan, epofenonane, fenoxycarb, hydroprene, kinoprene, methoprene, pyriproxifen, triprene 8. Ecdyson Agonists/Disruptors 8.1 Diacylhydrazines, for Example chromafenozide, halofenozide, methoxyfenozide, tebufenozide 9. Chitin Biosynthesis Inhibitors 9.1 Benzoylureas, for Example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron 9.2 Buprofezin 9.3 Cyromazine 10. Oxidative Phosphorylation Inhibitors, ATP Disruptors 10.1 Diafenthiuron 10.2 Organotins, for Example Azocyclotin, Cyhexatin, Fenbutatin-Oxide 11. Oxidative Phosphorylation Decouplers Acting by Interrupting the H-Proton Gradient 11.1 Pyrroles, for Example Chlorfenapyr 11.2 Dinitrophenols, for Example Binapacyrl, Dinobuton, Dinocap, DNOC 12. Side-I Electron Transport Inhibitors 12.1 METIs, for Example Fenazaquin, Fenpyroximate, Pyriridifen, Pyridaben, Tebufenpyrad, Tolfenpyrad 12.2 Hydramethylnon 12.3 Dicofol 13. Side-II Electron Transport Inhibitors Rotenone 14. Side-III Electron Transport Inhibitors Acequinocyl, fluacrypyrim 15. Microbial Disruptors of the Insect Gut Membrane

*Bacillus thuringiensis* strains

16. Fat Synthesis Inhibitors

Tetronic acids, for example spirodiclofen, spiromesifen

Tetramic acids, for example 3-(2,5-dimethylphenyl)-8-methoxy-2-oxo-1-azaspiro[4.5]dec-3-en-4-yl ethyl carbonate (aka: carbonic acid, 3-(2,5-dimethylphenyl)-8-methoxy-2-oxo-1-azaspiro[4.5]dec-3-en-4-yl ethyl ester, CAS-Reg.-No.: 382608-10-8) and carbonic acid, cis-3-(2,5-dimethylphenyl)-8-methoxy-2-oxo-1-azaspiro[4.5]dec-3-en-4-yl ethyl ester (CAS-Reg.-No.: 203313-25-1)

17. Carboxamides, for Example Flonicamid

18. Octopaminergic Agonists, for Example Amitraz

19. Inhibitors of Magnesium-Stimulated ATPase, for Example Propargite

20. BDCAs, for Example N2-[1,1-dimethyl-2-(methylsulphonyl)ethyl]-3-iodo-N1-[2-methyl-4-[1,2,2,2-tetrafluoro-1-(trifluoromethyl)ethyl]phenyl]-1,2-benzenedicarboxamide (CAS-Reg.-No.: 272451-65-7)

21. Nereistoxin Analogues, for Example Thiocyclam Hydrogen Oxalate, Thiosultap-Sodium 22. Biologicals, Hormones or Pheromones, for Example azadirachtin, *Bacillus* spec., *Beauveria* spec., codlemone, *Metarrhizium* spec., *Paecilomyces* spec., thuringiensin, *Verticillium* spec.

23. Active Compounds with Unknown or Unspecific Mechanisms of Action 23.1 Fumigants, for Example aluminium phosphide, methyl bromide, sulphuryl fluoride 23.2 Selective Antifeedants, for Example cryolite, flonicamid, pymetrozine 23.3 Mite Growth Inhibitors, for Example clofentezine, etoxazole, hexythiazox 23.4 Amidoflumet, Benclothiaz, Benzoximate, Bifenazate, Bromopropylate, Buprofezin, Quinomethionate, Chlordimeform, Chlorobenzilate, Chloropicrin, Clothiazoben, Cycloprene, Dicyclanil, Fenoxacrim, Fentrifanil, Flubenzimine, Flufenerim, Flutenzin, Gossyplure, Hydramethylnone, Japonilure, Metoxadiazone, Petroleum, Piperonyl Butoxide, Potassium Oleate, Pyridalyl, Sulfluramid, Tetradifon, Tetrasul, Triarathene, Verbutin, furthermore (1R-cis)-[5-(phenylmethyl)-3-furanyl]methyl-3-[(dihydro-2-oxo-3(2H)furanylidene)methyl]-2,2-dimethylcyclopropanecarboxylate (3-phenoxyphenyl)methyl-2,2,3,3-tetramethylcyclopropanecarboxylate 1-[(2-chloro-5-thiazolyl)methyl]tetrahydro-3,5-dimethyl-N-nitro-1,3,5-triazine-2(1H)-imine 2-(2-cbloro-6-fluorophenyl)-4-[4-(1,1-dimethylethyl)phenyl]4,5-dihydrooxazole 2-(acetyloxy)-3-dodecyl-1,4-naphthalenedione 2-chloro-N-[[[4-(1-phenylethoxy)phenyl]amino]carbonyl]benzamide 2-chloro-N-[[[4-(2,2-dichloro-1,1-difluoroethoxy)phenyl]amino]carbonyl]benzamide 3-methylphenyl propylcarbamate 4-[4-(4-ethoxyphenyl)-4-methylpentyl]-1-fluoro-2-phenoxybenzene 4-chloro-2-(1,1-dimethylethyl)-5-[[2-(2,6-dimethyl-4-phenoxyphenoxy)ethyl]thio]-3(2H)-pyridazinone 4-chloro-2-(2-chloro-2-methylpropyl)-5-[(6-iodo-3-pyridinyl)methoxy]-3(2H)-pyridazino 4-chloro-5-[(6-chlor-3-pyridinyl)methoxy]-2-(3,4-dichlorophenyl)-3(2H)-pyridazinone

*Bacillus thuringiensis* strain EG-2348 benzoic acid [2-benzoyl-1-(1,1-dimethylethyl)hydrazide butanoic acid 2,2-dimethyl-3-(2,4-dichlorophenyl)-2-oxo-1-oxaspiro[4.5]dec-3-en-4-yl ester

[3-[(6-chloro-3-pyridinyl)methyl]-2-thiazolidinylidene] cyanamide dihydro-2-(nitromethylene)-2H-1,3-thiazine-3(4H)-carboxaldehyde ethyl [2-[[1,6-dihydro-6-oxo-1-(phenylmethyl)-4-pyridazinyl]oxy]ethyl]carbamate N-(3,4,4-trifluoro-1-oxo-3-butenyl)glycine N-(4-chlorophenyl)-3-[4-(difluoromethoxy)phenyl]4,5-dihydro-4-phenyl-1H-pyrazole-1-carboxamide N-methyl-N'-(1-methyl-2-propenyl)-1,2-hydrazinedicarbothioamide N-methyl-N'-2-propenyl-1,2-hydrazinedicarbothioamide O,O-diethyl [2-(dipropylamino)-2-oxoethyl]ethylphosphoramidothioate A mixture with other known compounds such as herbicides, or with fertilizers and with growth regulators is also possible.

When employed as insecticides, the active compound combinations according to the invention, in their commercially available formulations and in the use forms prepared from these mixtures, may furthermore be present in a mixture with synergists. Synergists are compounds by which the activity of the active compounds is increased without it being necessary for the syngerist added to be active itself.

The active compound content of the use forms prepared from the commercially available formulations can vary within wide ranges. The active compound concentration of the use forms can be between 0.0000001 and 95% by weight of active compound, preferably between 0.0001 and 1% by weight.

They are applied in a customary manner adapted to suit the use forms.

When used against hygiene pests and stored-product pests, the active compound combinations are distinguished by an outstanding residual activity on wood and clay and by good stability to alkali on lime substrates.

The active compound combinations according to the invention act not only against plant pests, hygiene pests and stored-product pests, but also, in the veterinary medicine sector, against animal parasites (ectoparasites) such as hard ticks, soft ticks, mange mites, harvest mites, flies (stinging and licking), parasitic fly larvae, lice, hair lice, bird lice and fleas. These parasites include:

From the order of the *Anoplurida*, for example *Haematopinus* spp., *Linognathus* spp., *Pediculus* spp., *Phtirus* spp., *Solenopotes* spp.

From the order of the *Mallophagida* and the suborders Amblycerina and Ischnocerina, for example *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order *Diptera* and the suborders *Nematocerina* and *Brachycerina*, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the *Siphonapterida*, for example *Pulex* spp., *Ctenocephalides* spp., *Xenopsylla* spp., *Ceratophyllus* spp.

From the order of the *Heteropterida*, for example *Cimex* spp., *Triatoma* spp., *Rhodnius* spp., *Panstrongylus* spp.

From the order of the *Blattarida*, for example *Blatta orientalis, Periplaneta americana, Blattella germanica, Supella* spp.

From the subclass of the *Acari* (*Acarina*) and the orders of the Meta- and Mesostigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the *Actinedida* (*Prostigmata*) and *Acaridida* (*Astigmata*), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honeybees, other domestic animals such as, for example, dogs, cats, cage birds, aquarium fish and what are known as experimental animals such as, for example, hamsters, guinea pigs, rats and mice. By controlling these arthropods, it is intended to reduce deaths and reduce performance (in the case of meat, milk wool, hides, eggs, honey and the like), so that more economical and simpler animal keeping is made possible by the use of the active compound combinations according to the invention.

In the veterinary sector, the active compound combinations according to the invention are applied in the known manner by enteral administration in the form of, for example, tablets, capsules, drinks, drenches, granules, pastes, boluses, the feed-through method, suppositories, by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail marks, limb bands, halters, marking devices and the like.

When used for livestock, poultry, domestic animals and the like, the active compounds can be applied as formulations (for example powders, emulsions, flowables) which comprise the active compounds in an amount of from 1 to 80% by weight, either directly or after 100- to 10 000-fold dilution, or else as a chemical bath.

Furthermore, it has been found that the active compound combinations according to the invention have a potent insecticidal activity against insects which destroy industrial materials.

The following insects may be mentioned by way of example and by preference, but not by limitation:

Beetles such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Heminoptera such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristeltails such as *Lepisma saccharina.*

Industrial materials are understood as meaning, in the present context, non-live materials such as, preferably, polymers, adhesives, glues, paper and board, leather, wood, derived timber products and paints.

The material to be protected from attack by insects is very especially preferably wood and derived timber products.

Wood and derived timber products which can be protected by the composition according to the invention, or by mixtures comprising it, are understood as meaning, for example, construction timber, wooden beams, railway sleepers, bridge components, jetties; wooden vehicles, boxes, pallets, containers, telephone poles, wooden claddings, windows and doors made from wood, plywood, kitboard, joiners' work or wood-based materials which, quite generally, are used in domestic construction or in joinery.

The active compound combinations can be applied as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifer, dispersant and/or binder or fixative, water repellant, if appropriate desiccants and UV stabilizers and, if appropriate, colorants and pigments and other processing auxiliaries.

The insecticidal compositions or concentrates used for the protection of wood and derived timber products comprise the active compound according to the invention in a concentration of from 0.0001 to 95% by weight, in particular 0.001 to 60% by weight.

The amounts of compositions or concentrates employed depends on the species and the occurrence of the insects and on the medium. The optimum application rate can be determined for each application by test series. However, in general it will suffice to employ 0.0001 to 20% by weight, preferably 0.001 to 10% by weight, of active compound based on the material to be protected.

The solvent and/or diluent used is an organochemical or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents with an evaporation number of above 35 and a flashpoint of above 30° C., preferably above 45° C. Such water-insoluble, oily and oil-type solvents of low volatility which are used are suitable mineral oils or their aromatic fractions or mineral-oil-comprising solvent mixtures, preferably white spirit, petroleum and/or alkylbenzene.

Mineral oils which are preferably used are those with a boiling range of from 170 to 220° C., white spirit with a boiling range of 170 to 220° C., spindle oil with a boiling range of 250 to 350° C., petroleum and aromatics with a boiling range of from 160 to 280° C., oil of turpentine and the like.

In a preferred embodiment, liquid aliphatic hydrocarbons with a boiling range of from 180 to 210° C. or high-boiling mixtures of aromatic and aliphatic hydrocarbons with a boiling range of 180 to 220° C. and/or spindle oil and/or monochloronaphthalene are used, preferably α-monochloronaphthalene.

The organic oily or oil-type solvents of low volatility and with an evaporation number of above 35 and a flasbpoint of above 30° C., preferably above 45° C., can be replaced in part by organochemical solvents of high or medium volatility, with the proviso that the solvent mixture also has an evaporation number of above 35 and a flashpoint above 30° C., preferably above 45° C., and that the insecticide/fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin used as binder can be employed in the form of an emulsion, dispersion or solution. Bitumen or bituminous substances may also be used as binders in amounts of up to 10% by weight. In addition, colorants, pigments, water repellants, flavour-masking agents and inhibitors or anticorrosive agents and the like, all of which are known per se, can additionally be employed.

The composition or the concentrate preferably comprises, in accordance with the invention, at least one alkyd resin or modified alkyd resin and/or a drying vegetable oil as organochemical binder. Substances which are preferably used in accordance with the invention are alkyd resins with an oil content of over 45% by weight, preferably 50 to 68% by weight.

The abovementioned binder can be replaced fully or in part by a fixative (mixture) or a plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl) adipate, stearates such as butyl stearate or amyl stearate, oleates such as butyl oleate, glycerol ethers or high-molecular-weight glycol ethers, glycerol esters and p-toluenesulphonic esters.

Fixatives are based chemically on polyvinyl alkyl ethers such as, for example, polyvinyl methyl ether or ketones such as benzophenone, ethylenebenzophenone.

The solvent or diluent is, in particular, also water, if appropriate in a mixture with one or more of the abovementioned chemical solvents or diluents, emulsifiers and dispersants.

Particularly effective protection of timber is achieved by industrial-scale impregnating processes, for example the vacuum, the double-vacuum or pressure processes.

If appropriate, the ready-to-use compositions may additionally comprise further insecticides and, if appropriate, additionally one or more fungicides.

The active compound combinations according to the invention can at the same time be employed for protecting objects which come into contact with salt water or brackish water, in particular hulls, screens, nets, buildings, moorings and signalling system, against fouling.

Fouling sessile *Oligochaeta*, such as Serpulidae, and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., in particular fouling by sessile *Entomostraka* groups, which come under the generic term *Cirripedia* (cirriped crustaceans), is of particular importance Surprisingly, it has now been found that the active compound combinations according to the invention have an outstanding antifouling action.

Using the active compound combinations according to the invention allows the use of heavy metals such as, for example, in bis(trialkyltin) sulphides, tri-n-butyltin laurate, tri-n-butyltin chloride, copper(I) oxide, triethyltin chloride, tri-n-butyl (2-phenyl-4-chlorophenoxy)tin, tributylin oxide, molybdenum disulphide, antimony oxide, polymeric butyl titanate, phenyl-(bispyridine)bismuth chloride, tri-n-butyltin fluoride, manganese ethylenebis-thiocarbamate, zinc dimethyldithiocarabamate, zinc ethylenebisthiocarbamate, zinc salts and copper salts of 2-pyridinethiol 1-oxide, bisdimethyldithiocarbamoyl zinc ethylene-bisthiocarbamate, zinc oxide, copper (I) ethylenebisdithiocarbamate copper thiocyanate, copper naphthenate and tributyltin halides to be dispensed with or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3, 5-triazine, dichlorophen, diuron, endothal, fentin acetate, isoproturn, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propynyl butylcarbamate, tolylfluanid and azoles such as
azaconazole, cyproconazole, epoxyconazole, hexaconazole, metconazole, propiconazole and tebuconazole;

molluscicides such as
Fe complexing agents, fentin acetate, metaldehyde, methiocarb, niclosamid, thiodicarb and trimethacarb;

or conventional antifouling active compounds such as
4,5-dichloro-2-octyl-4-isothiazolin-3-one, diiodomethylparatryl sulphone 2-(N,N-dimethylthiocarbamoylthio)-5-nitrothiazyl, potassium, copper, sodium and zinc salts of 2-pyridinethiol 1-oxide, pyridinetriphenylborane, tetrabutyldistannoxane, 2,3,5,6-tetrachloro-4-(methylsulphonyl)pyridine, 2,4,5,6-tetrachloroisophthalonitrile, tetramethylthiuram disulphide and 2,4,6-trichlorophenylmaleiimide.

The antifouling compositions used comprise the active compound in a concentration of 0.001 to 50% by weight, in particular 0.01 to 20% by weight.

Moreover, the antifouling compositions comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscal and insecticidal active compounds, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compound combinations according to the invention may also be incorporated into self-polishing antifouling systems The active compound combinations according to the invention are also suitable for controlling animal pests, in particular insects, arachnids and mites, which are found in enclosed spaces such as for example, dwellings, factory halls, offices, drivers' cabins and the like. To control these pests they can be used in insecticidal products for domestic premises, either alone or in combination with other active compounds and auxiliaries. They are active against sensitive and resistant species and against all developmental stages. These pests include:

From the order of the Scorpionidea, for example *Buthus occitanus*.

From the order of the *Acarina*, for example *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example Aviculariidae, Araneidae.

From the order of the *Opiliones*, for example *Pseudoscorpiones chelifer, Pseudoscorpiones cheiridium, Opiliones phalangium*.

From the order of the *Isopoda*, for example *Oniscus asellus, Porcellio scaber*.

From the order of the *Diplopoda*, for example *Blaniulus guttulatus, Polydesmus* spp.

From the order of the *Chilopoda*, for example *Geophilus* spp.

From the order of the *Zygentoma*, for example *Ctenolepisma* spp., *Lepisma saccharina, Lepismodes inquilinus*.

From the order of the *Blattaria*, for example *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the *Saltatoria*, for example *Acheta domesticus*.

From the order of the *Dermaptera*, for example *Forficula auricularia*.

From the order of the *Isoptera*, for example *Kalotermes* spp., *Reticuliternes* spp.

From the order of the *Psocoptera*, for example *Lepinatus* spp., *Liposcelis* spp.

From the order of the *Coleptera*, for example *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the *Diptera*, for example *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the *Lepidoptera*, for example *Achroia grisella, Galleria mellonella, Plodia interpunctella, Tinea cloacella, Tinea pellionella, Tineola bisselliella*.

From the order of the *Siphonaptera*, for example *Ctenocephalides canis, Ctenocephalides felis, Pulex irritans, Tunga penetrans, Xenopsylla cheopis*.

From the order of the *Hymenoptera*, for example *Camponotus herculeanus, Lasius fuliginosus, Lasius niger, Lasius umbratus, Monomorium pharaonis, Paravespula* spp., *Tetramorium caespitum*.

From the order of the *Anoplura*, for example *Pediculus humanus capitis, Pediculus humanus corporis, Phthirus pubis*.

From the order of the *Heteroptera*, for example *Cimex hemipterus, Cimex lectularius, Rhodinus prolixus, Triatoma infestans*.

The application in the field of the domestic insecticides may also be carried out in combination with other suitable active compounds such as phosphoric esters, carbamates, pyrethroids, growth regulators or active compounds from other known classes of insecticides.

The application is carried out in aerosols, unpressurized sprays, for example pump sprays and atomizer sprays, automatic misting devices, foggers, foams, gels, vaporizer products with vaporizer platelets made of cellulose or polymer, liquid vaporizers, gel and membrane vaporizers, propeller-driven vaporizers, vaporization systems which do not consume energy passive vaporization systems), moth papers, moth sachets and moth gels in the form of granules or dusts, in baits for scattering or bait stations.

When employing the active compound combinations according to the invention, the application rates can be varied within a substantial range, depending on the type of application. In the case of the treatment of plant parts, the application rates of active compound combination are generally between 0.1 and 10 000 g/ha, preferably between 10 and 1 000 g/ha.

The good insecticidal activity of the active compound combinations according to the invention can be seen from the examples which follow. While the individual active compounds show weaknesses in their activity, combinations demonstrate an activity which exceeds a simple additive effect.

The activity to be expected for a given combination of two combinations can be calculated as follows (cf. COLBY, S. R.; "Calculating synergistic and antagonistic responses of herbicide combinations", Weeds 15, pages 20-22, 1967);

if

X=activity in %, destruction in comparison with the untreated control by compound A (active compound of the formula I) at a concentration of m ppm and Y=activity in %, destruction in comparison with the untreated control by compound B (active compound of the formula I) at a concentration of n ppm and E=efficacy in %, destruction in comparison with the untreated control when the mixture A and B is applied at m and n ppm, $$\text{then } E = X + Y - \frac{X \times Y}{100}$$

If the actual damage exceeds the calculated figure, the activity of the combination is superadditive, that is to say it demonstrates a synergistic effect.

EXAMPLE A

| Aphis gossypii test | |
|---|---|
| Solvent: | 7 parts by weight of dimethylformamide |
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cotton leaves (Gossypium hirsutum) which are severely infested with cotton aphids (Aphis gossypii) are treated by being dipped into the active compound preparation of the desired concentration.

After the desired period of time, the destruction is determined in %. In this context, 100% means that all of the aphids were destroyed; 0% means that no aphids were destroyed.

Results achieved in this test are shown in the table which follows.

TABLE A

Plant-injurious insects
Aphis gossypii test

| Active compounds | Active compound concentration in ppm | Destruction in % after 6 d | |
|---|---|---|---|
| Thiacloprid | 0.8 | 25 | |
| Clothianidin | 0.8 | 0 | |
| | | found* | calc.** |
| Thiacloprid + clothianidin (1:1) according to the invention | 0.8 + 0.8 | 98 | 25 |

*found = actual insecticidal activity
**calc. = activity calculated using Colby's formula

EXAMPLE B

| Bemisia tabaci test | |
|---|---|
| Solvent: | 7 parts by weight of dimethylformamide |
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cotton plants (Gossypium hirsutum) which are infested with whitefly (Bemisia tabaci) eggs, larvae and puparia are sprayed with the active compound preparation of the desired concentration.

After the desired period of time, the destruction is determined in %. In this context, 100% means that all of the whiteflies were destroyed; 0% means that no whiteflies were destroyed.

Results achieved in this test are shown in the table which follows.

TABLE B

Plant-injurious insects
Bemisia tabaci test

| Active compounds | Active compound concentration in ppm | Destruction in % after 12 d | |
|---|---|---|---|
| Thiacloprid | 0.8 | 80 | |
| Clothianidin | 0.8 | 35 | |
| | | found* | calc.** |
| Thiacloprid + clothianidin (1:1) according to the invention | 0.8 + 0.8 | 92.5 | 87 |

*found = actual insecticidal activity
**calc. = activity calculated using Colby's formula

| Heliothis armigera test | |
|---|---|
| Solvent: | 7 parts by weight of dimethylformamide |
| Emulsifier: | 2 parts by weight of alkylaryl polyglycol ether |

EXAMPLE C

To prepare a suitable active compound preparation, 1 part by weight of active compound is mixed with the stated amounts of solvent and emulsifier, and the concentrate is diluted with emulsifier-comprising water to the desired concentration.

Soya bean shoots (Glycine max) are treated by being dipped into the active compound preparation of the desired concentration and populated with Heliothis armigera caterpillars while the leaves are still damp.

After the desired period of time, the destruction is determined in %. In this context, 100% means that all of the caterpillars were destroyed; 0% means that no caterpillars were destroyed.

Results achieved in this test are shown in the table which follows.

TABLE C

Plant-injurious insects
Heliothis armigera test

| Active compounds | Active compound concentration in ppm | Destruction in % after 6 d | |
|---|---|---|---|
| Thiacloprid | 4 | 35 | |
| Clothianidin | 4 | 45 | |
| | | found* | calc.** |
| Thiacloprid + clothianidin (1:1) according to the invention | 4 + 4 | 90 | 64.25 |

*found = actual insecticidal activity
**calc. = activity calculated using Colby's formula

EXAMPLE D

| Myzus persicae test | |
|---|---|
| Solvent: | 7 parts by weight of dimethylformamide |
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cabbage leaves (Brassica oleracea) which are severely infested with green peach aphids (Myzus persicae) are treated by being dipped into the active compound preparation of the desired concentration.

After the desired period of time, the destruction is determined in %. In this context, 100% means that all of the aphids were destroyed; 0% means that no aphids were destroyed.

Results achieved in this test are shown in the table which follows.

TABLE D

Plant-injurious insects
Myzus persicae test

| Active compounds | Active compound concentration in ppm | Destruction in % after 6 d | |
|---|---|---|---|
| Thiacloprid | 0.8 | 20 | |
| Clothianidin | 0.8 | 65 | |
| | | found* | calc.** |
| Thiacloprid + clothianidin (1:1) according to the invention | 0.8 + 0.8 | 95 | 72 |

*found = actual insecticidal activity
**calc. = activity calculated using Colby's formula

EXAMPLE E

| Plutella xylostella test (normal strain) | |
|---|---|
| Solvent: | 7 parts by weight of dimethylformamide |
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cabbage leaves (Brassica oleracea) are treated by being dipped into the active compound preparation of the desired concentration and populated with diamondback moth caterpillars (Plutella xylostella/sensitive strain) while the leaves are still moist.

After the desired period of time, the destruction is determined in %. In this context, 100% means that all of the caterpillars were destroyed; 0% means that no caterpillars were destroyed.

Results achieved in this test are shown in the table which follows.

TABLE E

Plant-injurious insects
Plutella xylostella test (normal strain)

| Active compounds | Active compound concentration in ppm | Destruction in % after 6 d | |
|---|---|---|---|
| Thiacloprid | 20 | 15 | |
| Clothianidin | 20 | 60 | |
| | | found* | calc.** |
| Thiacloprid + clothianidin (1:1) according to the invention | 20 + 20 | 100 | 66 |

*found = actual insecticidal activity
**calc. = activity calculated using Colby's formula

EXAMPLE F

| Heliothis armigera test | |
|---|---|
| Solvent: | 7 parts by weight of dimethylformamide |
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Soya bean shoots (glycine max) are treated by being dipped into the active compound preparation of the desired concentration and populated with Heliothis armigera caterpillars while the leaves are still moist.

After the desired period of time, the destruction is determined in %. In this context, 100% means that all of the caterpillars were destroyed; 0% means that no caterpillars were destroyed.

Results achieved in this test are shown in the table which follows.

TABLE F

Plant-injurious insects Heliothis armigera test

| Active compounds | Active compound concentration in ppm | Destruction in % after 7 d | |
|---|---|---|---|
| Imidacloprid | 4 | 10 | |
| Thiacloprid | 0.8 | 0 | |
| | | found* | calc.** |
| Imidacloprid + thiacloprid (5:1) according to the invention | 4 + 0.8 | 20 | 10 |

*found = actual insecticidal activity
**calc. = activity calculated using Colby's formula

EXAMPLE G

Myzus test

| | |
|---|---|
| Solvent: | 7 parts by weight of dimethylformamide |
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cabbage leaves (*Brassica oleracea*) which are severely infested with green peach aphids (*Myzus persicae*) are treated by being dipped into the active compound preparation of the desired concentration.

After the desired period of time, the destruction is determined in %. In this context, 100% means that all of the aphids were destroyed; 0% means that no aphids were destroyed.

Results achieved in this test are shown in the table which follows.

TABLE G

| | Plant-injurious insects *Myzus* test | | |
|---|---|---|---|
| Active compounds | Active compound concentration in ppm | Destruction in % after 6 d | |
| Imidacloprid | 0.16 | 10 | |
| Thiacloprid | 0.16 | 10 | |
| | | found* | calc.** |
| Imidacloprid + thiacloprid (1:1) according to the invention | 0.16 + 0.16 | 30 | 19 |

*found = actual insecticidal activity
**calc. = activity calculated using Colby's formula

EXAMPLE H

Plutella test (normal strain)

| | |
|---|---|
| Solvent: | 7 parts by weight dimethylformamide |
| Emulsifier: | 2 parts by weight alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cabbage leaves (*Brassica oleracea*) are treated by being dipped into the active compound preparation of the desired concentration and populated with diamondback moth caterpillars (*Plutella xylostella*/normal strain) while the leaves are still moist.

After the desired period of time, the destruction is determined in %. In this context, 100% means that all of the caterpillars were destroyed; 0% means that no caterpillars were destroyed.

Results achieved in this test are shown in the table which follows.

TABLE H

| | Plant-injurious insects *Plutella* test (normal strain) | | |
|---|---|---|---|
| Active compounds | Active compound concentration in ppm | Destruction in % after 7 d | |
| Imidacloprid | 20 | 15 | |
| Thiacloprid | 4 | 0 | |
| | | found* | calc.** |
| Imidacloprid + thiacloprid (5:1) according to the invention | 20 + 4 | 55 | 15 |

*found = actual insecticidal activity
**calc. = activity calculated using Colby's formula

EXAMPLE I

Spodoptera exigua test

| | |
|---|---|
| Solvent: | 7 parts by weight of dimethylformamide |
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cabbage leaves (*Brassica oleracea*) are treated by being dipped into the active compound preparation of the desired concentration and populated with army worm caterpillars (*Spodoptera exigua*) while the leaves are still moist.

After the desired period of time, the destruction is determined in %. In this context, 100% means that all of the caterpillars were destroyed; 0% means that no caterpillars were destroyed.

Results achieved in this test are shown in the table which follows.

TABLE I

| | Plant-injurious insects *Spodoptera exigua* test | | |
|---|---|---|---|
| Active compounds | Active compound concentration in ppm | Destruction in % after 7 d | |
| Imidacloprid | 100 | 45 | |
| Thiacloprid | 100 | 0 | |
| | | found* | calc.** |
| Imidacloprid + thiacloprid (1:1) according to the invention | 100 + 100 | 55 | 45 |

*found = actual insecticidal activity
**calc. = activity calculated using Colby's formula

EXAMPLE J

| Spodoptera frugiperda test | |
|---|---|
| Solvent: | 7 parts by weight of dimethylformamide |
| Emulsifier: | 2 parts by weight alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cabbage leaves (Brassica oleracea) are treated by being dipped into the active compound preparation of the desired concentration and populated with army worm caterpillars (Spodoptera frugiperda) while the leaves are still moist.

After the desired period of time, the destruction is determined in %. In this context, 100% means that all of the caterpillars were destroyed; 0% means that no caterpillars were destroyed.

Results achieved in this test are shown in the table which follows.

TABLE J

Plant-injurious insects
Spodoptera frugiperda test

| Active compounds | Active compound concentration in ppm | Destruction in % after 7 d | |
|---|---|---|---|
| Imidacloprid | 0.8 | 20 | |
| Thiacloprid | 0.8 | 10 | |
| | | found* | calc.** |
| Imidacloprid + thiacloprid (1:1) according to the invention | 0.8 + 0.8 | 40 | 28 |

*found = actual insecticidal activity
**calc. = activity calculated using Colby's formula

EXAMPLE K

| Bemisia tabaci test | |
|---|---|
| Solvent: | 7 parts by weight of dimethylformamide |
| Emulsifier: | 2 parts by weight alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cotton plants (Gossypium hirsutum) which are infested with whitefly (Bemisia tabaci) eggs, larvae and puparia are sprayed with the active compound preparation of the desired concentration.

After the desired period of time, the destruction is determined in %. In this context, 100% means that all of the whiteflies were destroyed; 0% means that no whiteflies were destroyed.

Results achieved in this test are shown in the table which follows.

TABLE K

Plant-injurious insects
Bemisia tabaci test

| Active compounds | Active compound concentration in ppm | Destruction in % after 10 d | |
|---|---|---|---|
| Imidacloprid | 0.16 | 5 | |
| Clothianidin | 0.16 | 5 | |
| | | found* | calc.** |
| Imidacloprid + clothianidin (1:1) according to the invention | 0.16 + 0.16 | 35 | 9.75 |

*found = actual insecticidal activity
**calc. = activity calculated using Colby's formula

EXAMPLE L

| Heliothis armigera test | |
|---|---|
| Solvent: | 7 parts by weight of dimethylformamide |
| Emulsifier: | 2 parts by weight alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Soya bean shoots (Glycine max) are treated by being dipped into the active compound preparation of the desired concentration and populated with Heliothis armigera caterpillars while the leaves are still moist.

After the desired period of time, the destruction is determined in %. In this context, 100% means that all of the caterpillars were destroyed; 0% means that no caterpillars were destroyed.

Results achieved in this test are shown in the table which follows.

TABLE L

Plant-injurious insects
Heliothis armigera test

| Active compounds | Active compound concentration in ppm | Destruction in % after 6 d | |
|---|---|---|---|
| Imidacloprid | 4 | 10 | |
| Clothianidin | 4 | 0 | |
| | | found* | calc.** |
| Imidacloprid + clothianidin (1:1) according to the invention | 4 + 4 | 70 | 10 |

*found = actual insecticidal activity
**calc. = activity calculated using Colby's formula

EXAMPLE M

| Myzus persicae test | |
|---|---|
| Solvent: | 7 parts by weight of dimethylformamide |
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cabbage leaves (*Brassica oleracea*) which are severely infested with green peach aphids (*Myzus persicae*) are treated by being dipped into the active compound preparation of the desired concentration.

After the desired period of time, the destruction is determined in %. In this context, 100% means that all of the aphids were destroyed; 0% means that no aphids were destroyed.

Results achieved in this test are shown in the table which follows.

TABLE M

| | Plant-injurious insects *Myzus persicae* test | | |
|---|---|---|---|
| Active compounds | Active compound concentration in ppm | Destruction in % after 6 d | |
| | | found* | calc.** |
| Imidacloprid | 0.16 | 50 | |
| Clothianidin | 0.16 | 0 | |
| Imidacloprid + clothianidin (1:1) according to the invention | 0.16 + 0.16 | 70 | 50 |

*found = actual insecticidal activity
**calc. = activity calculated using Colby's formula

EXAMPLE N

| *Spodoptera exigua* test | |
|---|---|
| Solvent: | 7 parts by weight of dimethylformamide |
| Emulsifier: | 2 parts by weight alkylaryl polyglycol ether |

To prepare a suitable active compound preparation, 1 part by weight of active compound is mixed with the stated amounts of solvent and emulsifier, and the concentrate is diluted with emulsifier-comprising water to the desired concentration.

Cabbage leaves (*Brassica oleracea*) are treated by being dipped into the active compound preparation of the desired concentration and populated with army worm caterpillars (*Spodoptera exigua*) while the leaves are still moist.

After the desired period of time, the destruction is determined in %. In this context, 100% means that all of the caterpillars were destroyed; 0% means that no caterpillars were destroyed.

Results achieved in this test are shown in the table which follows.

TABLE N

| | Plant-injurious insects *Spodoptera exigua* test | | |
|---|---|---|---|
| Active compounds | Active compound concentration in ppm | Destruction in % after 6 d | |
| | | found* | calc.** |
| Imidacloprid | 20 | 10 | |
| Clothianin | 20 | 10 | |
| Imidacloprid + clothianin (1:1) according to the invention | 20 + 20 | 70 | 19 |

*found = actual insecticidal activity
**calc. = activity calculated using Colby's formula

The invention claimed is:

1. A method for controlling insects, arachnids, or nematodes in agriculture, comprising contacting said insects, arachnids, nematodes, or their habitat with a synergistic mixture of imidacloprid and clothianidin, wherein the weight ratio of imidacloprid to clothianidin is from 10:1 to 1:10.

2. A method according to claim 1, wherein said contacting comprising contacting seeds of plants.

3. A method according to claim 1, wherein the weight ratio of imidacloprid to clothianidin is 1 to 1.

4. A synergistic composition comprising imidacloprid and clothianidin, and, optionally, one or more extenders, one or more surface-active substances, or a combination of one or more extenders and one or more surface-active substances, wherein the weight ratio of imidacloprid to clothianidin is from 10:1 to 1:10.

5. A method for protecting seeds or growing plants, comprising contacting said seeds or said growing plants with a composition according to claim 4.

6. A seed treated with a composition according to claim 4.

7. A method of controlling animal pests, comprising contacting said animal pests with a composition according to claim 4.

8. A synergistic composition according to claim 4, wherein the weight ratio of imidacloprid to clothianidin is 1 to 1.

9. A method for preparing pesticides, comprising mixing imidacloprid and clothianidin together with one or more extenders, one or more surface-active substances, or a combination of one or more extenders and one or more surface-active substances, wherein the weight ratio of imidacloprid to clothianidin is from 10:1 to 1:10.

10. A method according to claim 9, wherein the weight ratio of imidacloprid to clothianidin is 1 to 1.

* * * * *